(12) United States Patent
Davis et al.

(10) Patent No.: US 7,981,074 B2
(45) Date of Patent: Jul. 19, 2011

(54) IRRIGATION/ASPIRATION SYSTEM

(75) Inventors: Sherman G. Davis, Laguna Niguel, CA (US); Gary P. Sorensen, Lake Forest, CA (US)

(73) Assignee: Novartis AG, Basel (CH)

( * ) Notice: Subject to any disclaimer, the term of this patent is extended or adjusted under 35 U.S.C. 154(b) by 464 days.

(21) Appl. No.: 11/591,980

(22) Filed: Nov. 2, 2006

(65) Prior Publication Data

US 2008/0125699 A1    May 29, 2008

(51) Int. Cl.
    *A61M 1/00* (2006.01)
(52) U.S. Cl. .......................................... 604/35; 604/118
(58) Field of Classification Search .................. 604/35, 604/118, 174–180, 294
    See application file for complete search history.

(56) References Cited

U.S. PATENT DOCUMENTS

| | | |
|---|---|---|
| 3,336,764 A | 8/1967 | Chambers |
| 3,589,363 A | 6/1971 | Banko |
| 3,994,297 A | 11/1976 | Kopf |
| 3,997,097 A | 12/1976 | Embury |
| 4,223,676 A | 9/1980 | Wuchinich |
| 4,246,902 A | 1/1981 | Martinez |
| 4,493,694 A | 1/1985 | Wuchinich |
| 4,515,583 A | 5/1985 | Sorich |
| 4,553,957 A | 11/1985 | Williams et al. |
| 4,589,415 A | 5/1986 | Haaga |
| 4,609,368 A | 9/1986 | Dotson, Jr. |
| 4,627,844 A | 12/1986 | Schmitt |
| 4,662,404 A | 5/1987 | LeVeen et al. |
| 4,750,902 A | 6/1988 | Wuchinich et al. |
| 4,816,018 A | 3/1989 | Parisi |
| 4,869,715 A | 9/1989 | Sherburne |
| 4,922,902 A | 5/1990 | Wuchinich |
| 4,954,055 A | 9/1990 | Raible et al. |
| 4,989,583 A | 2/1991 | Hood |
| 5,154,694 A | 10/1992 | Kelman |
| 5,261,885 A * | 11/1993 | Lui ............................... 604/247 |
| 5,318,515 A | 6/1994 | Wilk |
| 5,340,330 A | 8/1994 | Dolson et al. |
| 5,359,996 A | 11/1994 | Hood |
| 5,399,160 A * | 3/1995 | Dunberger et al. ............. 604/31 |
| 5,476,448 A | 12/1995 | Urich |
| 5,533,878 A | 7/1996 | Iwata |
| 5,549,547 A | 8/1996 | Cohen et al. |
| 5,616,120 A | 4/1997 | Andrew et al. |
| 5,662,144 A | 9/1997 | Lo et al. |
| 5,685,841 A * | 11/1997 | Mackool ......................... 604/22 |
| 5,700,240 A | 12/1997 | Barwick et al. |
| 5,704,401 A | 1/1998 | Fukui et al. |

(Continued)

FOREIGN PATENT DOCUMENTS

DE    3942192 A1 *    6/1991

(Continued)

OTHER PUBLICATIONS

Peterson, Robert, Varying Material Properties of a Single Fluidic Line in Ophthalmology Tubing, U.S. Appl. No. 12/204,284, filed Aug. 27, 2009, 14 pages.

(Continued)

*Primary Examiner* — Theodore J Stigell
*Assistant Examiner* — Imani Hayman

(57) ABSTRACT

A surgical system with irrigation and aspiration lines having different compliance or stiffness, with the irrigation line having a higher compliance than the aspiration line.

15 Claims, 3 Drawing Sheets

U.S. PATENT DOCUMENTS

| | | | |
|---|---|---|---|
| 5,873,851 A * | 2/1999 | Nilsson | 604/43 |
| 5,897,537 A | 4/1999 | Berg et al. | |
| 5,988,700 A | 11/1999 | Prichard | |
| 6,050,971 A | 4/2000 | Garnier et al. | |
| 6,159,175 A * | 12/2000 | Strukel et al. | 604/22 |
| 6,283,974 B1 | 9/2001 | Alexander | |
| 6,579,259 B2 * | 6/2003 | Stevens et al. | 604/96.01 |
| 6,599,271 B1 | 7/2003 | Easley | |
| 6,629,948 B2 | 10/2003 | Rockley et al. | |
| 6,878,142 B2 * | 4/2005 | Lawrence et al. | 604/540 |
| 6,913,041 B2 | 7/2005 | Lehnhardt et al. | |
| 6,960,182 B2 | 11/2005 | Moutafis et al. | |
| 7,172,578 B2 | 2/2007 | Mackool | |
| 7,371,224 B2 | 5/2008 | Haischmann et al. | |
| 7,484,769 B2 | 2/2009 | Domash et al. | |
| 2002/0022810 A1 | 2/2002 | Urich | |
| 2002/0055725 A1 | 5/2002 | Verkaart et al. | |
| 2002/0128560 A1 | 9/2002 | Urich | |
| 2003/0195460 A1 | 10/2003 | Kadziauskas | |
| 2004/0034333 A1 | 2/2004 | Seese et al. | |
| 2004/0039351 A1 | 2/2004 | Barrett | |
| 2004/0116901 A1 | 6/2004 | Appling | |
| 2005/0070859 A1 | 3/2005 | Cull et al. | |
| 2005/0080375 A1 | 4/2005 | Kadziauskas et al. | |
| 2005/0135974 A1 | 6/2005 | Harvey et al. | |
| 2006/0041220 A1 | 2/2006 | Boukhny et al. | |
| 2006/0084937 A1 | 4/2006 | Akahoshi | |
| 2006/0135974 A1 | 6/2006 | Perkins | |
| 2006/0161101 A1 | 7/2006 | Dimalanta et al. | |
| 2006/0173404 A1 | 8/2006 | Urich et al. | |
| 2006/0224163 A1 * | 10/2006 | Sutton | 606/107 |
| 2006/0253062 A1 | 11/2006 | Liao et al. | |
| 2006/0293646 A1 | 12/2006 | Whayne et al. | |
| 2007/0032777 A1 | 2/2007 | Perkins et al. | |
| 2007/0043338 A1 * | 2/2007 | Moll et al. | 606/1 |
| 2007/0043351 A1 * | 2/2007 | Fleischman et al. | 606/49 |
| 2007/0070859 A1 | 4/2007 | Cull et al. | |
| 2007/0078440 A1 | 4/2007 | Perkins et al. | |
| 2007/0098578 A1 | 5/2007 | Morgan | |
| 2007/0149919 A1 | 6/2007 | Perkins et al. | |
| 2007/0149950 A1 | 6/2007 | Perkins et al. | |
| 2007/0250040 A1 | 10/2007 | Provost et al. | |
| 2007/0267012 A1 | 11/2007 | McCarthy | |
| 2008/0125699 A1 | 5/2008 | Davis et al. | |
| 2008/0300539 A1 | 12/2008 | Vreeman et al. | |
| 2010/0056991 A1 | 3/2010 | Dimalanta, Jr. et al. | |
| 2010/0057092 A1 | 3/2010 | Peterson | |

FOREIGN PATENT DOCUMENTS

| | | |
|---|---|---|
| DE | 10233053 A1 | 2/2004 |
| DE | 10233053 B4 | 2/2005 |
| EP | 1716828 A1 | 11/2006 |
| EP | 1716828 B1 | 5/2008 |
| EP | 1917987 A2 | 5/2008 |
| EP | 1917987 A3 | 8/2008 |
| EP | 1917987 B1 | 12/2009 |
| EP | 2161046 A1 | 3/2010 |
| FR | 964069 | 8/1950 |
| JP | 10-071166 A | 3/1998 |
| JP | 05-305096 A | 11/1999 |
| WO | 9807398 | 2/1998 |
| WO | WO 99/38549 A1 | 8/1999 |
| WO | WO 01/74427 A1 | 10/2001 |
| WO | WO 2006/069016 | 6/2006 |

OTHER PUBLICATIONS

Dimalanta, Ramon, et al., Multi-Compliant Tubing, U.S. Appl. No. 12/540,014, filed Aug. 12, 2009, 32 pages.

European Patent Office, European Search Report, European Patent Application No. EP 09 17 5773.2, Jan. 28, 2010, 5 pages.

Kishimoto, Makoto, MD, Opesaver-Super Irrigation System, Techniques in Ophthalmology, Mar. 2006, 6 pages, vol. 4, Issue 1, Lippincott Williams & Wilkins, Shiga, Japan.

Ruckert, Wolfgang, "Contribution to the Development of an Elastic Lens with a Variable Focal Length for Use in an Artificial Accommodation System," Dissertation, [published after Nov. 2, 2006], 9 pages, Karlsruhe University Press, pp. 25-27.

Dr. Ulrich Naumann, Notice of Opposition and EPO Communication, Sep. 23, 2010, 25 pages European Search Report—EP 1 917 987.

Publication No. 2010/0057092, Office Action Mailed Oct. 7, 2010 and Response filed Jan. 7, 2011, 31 pages.

* cited by examiner

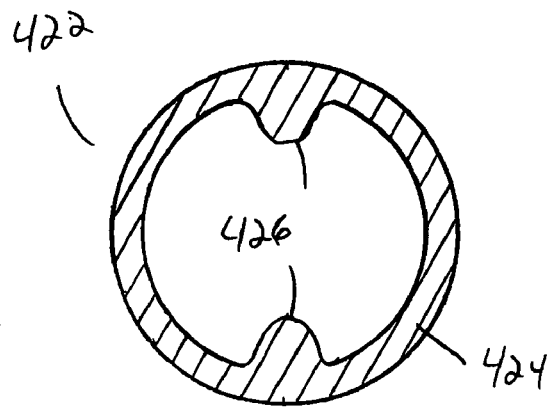
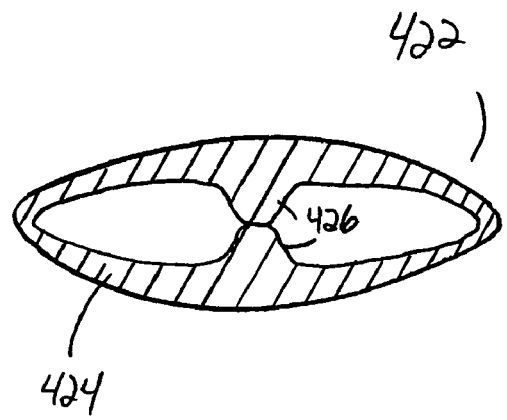
FIG. 7        FIG. 8
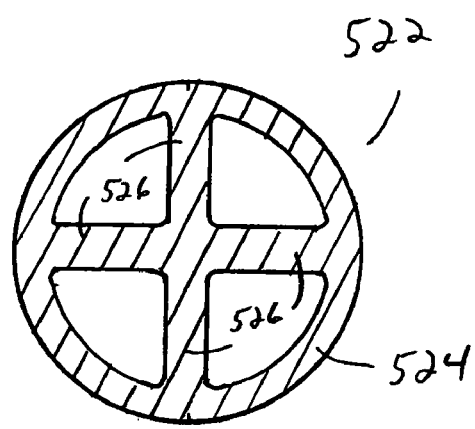
FIG. 9

IRRIGATION/ASPIRATION SYSTEM

BACKGROUND OF THE INVENTION

This invention relates generally to the field of phacoemulsification and more particularly to irrigation/aspiration ("I/A") systems used during phacoemulsification.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an IOL.

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

One possible complication associated with cataract surgery is anterior chamber collapse following an occlusion break. Occlusion of the phacoemulsification tip can occur when a piece of lens material fully covers the distal aspiration port. When an occlusion occurs, vacuum can build in the system aspiration line so that when the occlusion eventually breaks, a sudden surge occurs, drawing fluid and lens material out of the eye and into tip aspiration port. When fluid is draw out of the eye faster than it can be replaced, the eye can soften and collapse.

One way to reduce surge after an occlusion break is to reduce the compliance in the aspiration system. By reducing compliance, vacuum build-up during an occlusion is reduced. However, as flexible tubings are used to connect the handpiece to the surgical console, there will always be some compliance in the aspiration system.

Another prior art method involves increasing the size of the irrigation line. While not addressing the size of any post-occlusion fluid surge directly, a larger irrigation line allows for large irrigation fluid flows, so that any vacuum build-up in the eye is more easily quenched, thereby reducing the risk of anterior chamber collapse. Larger irrigation lines, however, can make the handpiece more difficult to hold and control.

Therefore, a need continues to exist for a simple and reliable irrigation/aspiration system that reduces fluid flow surges.

BRIEF SUMMARY OF THE INVENTION

The present invention improves upon the prior art by providing a surgical system with irrigation and aspiration lines having different compliance or stiffness, with the irrigation line having a higher compliance than the aspiration line.

Accordingly, one objective of the present invention is to provide an irrigation/aspiration system having a relatively compliant irrigation line.

Another objective of the present invention is to provide a method to reduce post occlusion break surge.

These and other advantages and objectives of the present invention will become apparent from the detailed description and claims that follow.

BRIEF DESCRIPTION OF THE DRAWINGS

FIG. 7 is a cross-sectional view of a fifth embodiment of an irrigation line that may be used with the present invention shown expanded.

FIG. 8 is a cross-sectional view of the fifth embodiment of an irrigation line illustrated in FIG. 7 shown collapsed.

FIG. 9 is a cross-sectional view of a sixth embodiment of an irrigation line that may be used with the present invention.

DETAILED DESCRIPTION OF THE INVENTION

Figure 1:
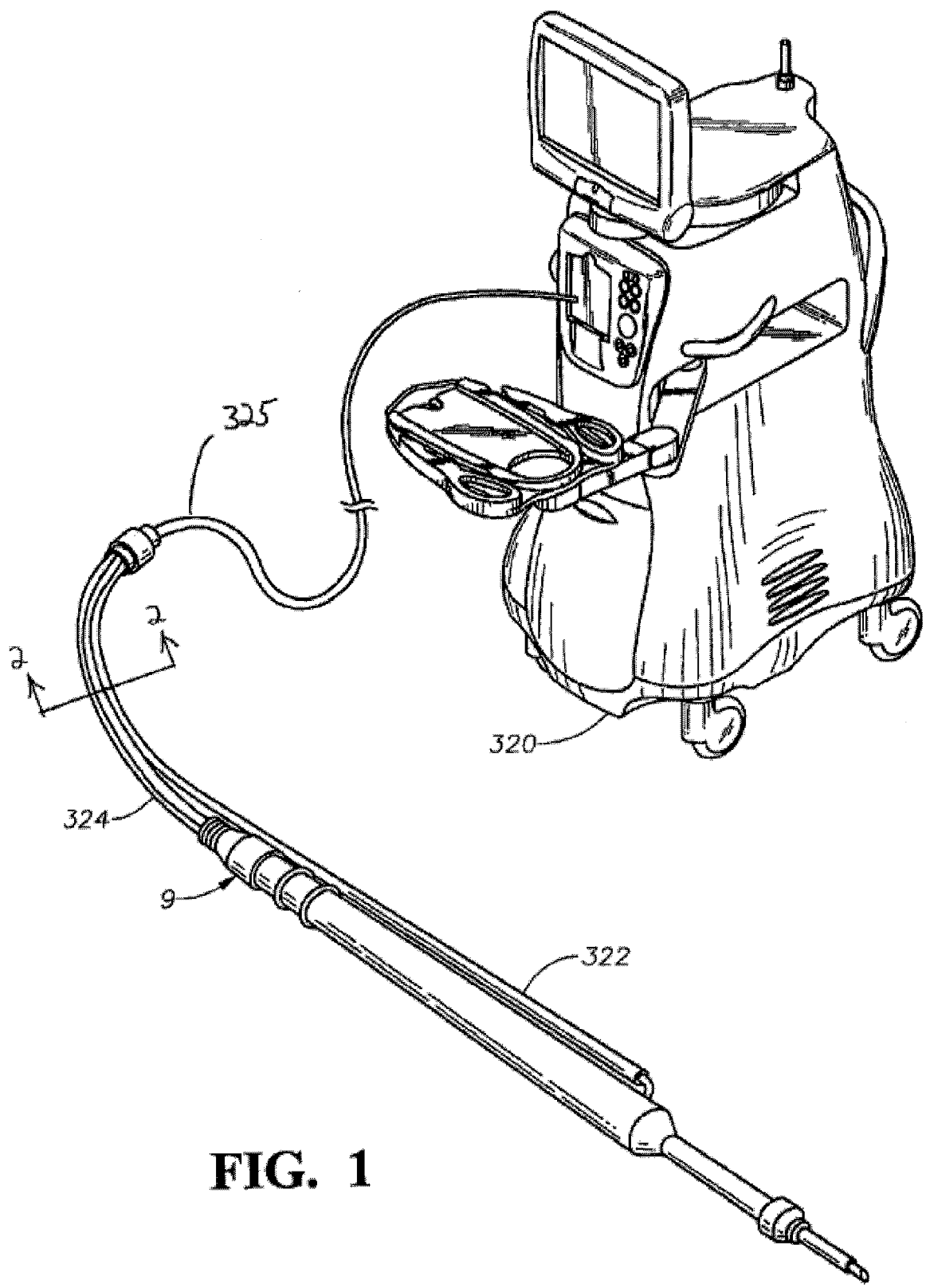
FIG. 1 is a perspective view of a handpiece and control console that may be used with the present invention.

As best seen in FIG. 1, surgical console 320 suitable for use with the present invention may be any commercially available surgical control console such as the INFINITI® Vision System available from Alcon Laboratories, Inc., Fort Worth, Tex. Console 320 is connected to handpiece 9 through irrigation line 322 and aspiration line 324, and the flow through lines 322 and 324 is controlled by the user, for example, via a footswitch or a wireless remote control (not shown). Aspiration line 324 and irrigation line 322 generally are constructed from a flexible material such as PVC or silicone rubber.

Figure 2:
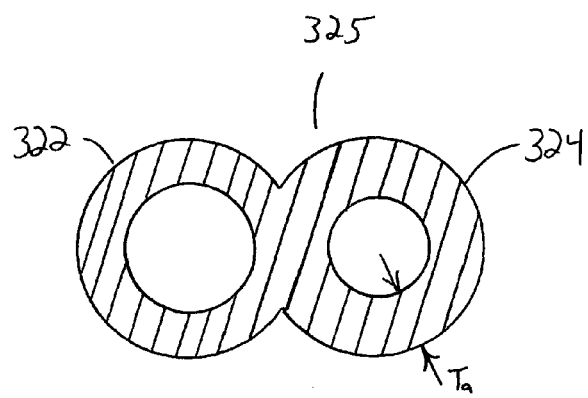
FIG. 2 is an enlarged cross-section view of a prior art irrigation/aspiration line taken at line 2-2 in FIG. 1.

As best seen in FIG. 2, currently available irrigation line 322 and aspiration line 324 are extruded as single line 325 from a common material. The compliance in aspiration line 324 is reduced by increasing wall thickness $T_a$ relative to irrigation line 322. Alternatively, or in addition, aspiration line 324 can be made from a material having a relatively higher stiffness, or durometer, for example, on the order of between 75 shore A and 100 shore A durometer. As aspiration line 324 and irrigation line 322 are co-extruded, increasing the stiffness of aspiration line 324 results in a stiffer irrigation line.

Figure 3:
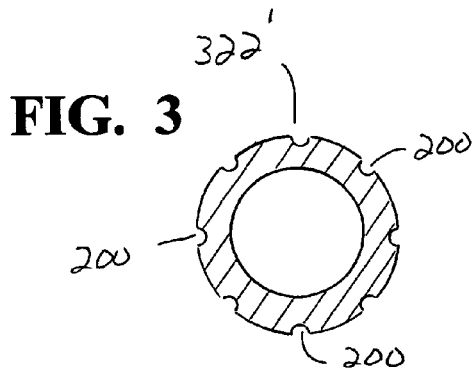
FIG. 3 is a cross-sectional view of a first embodiment of an irrigation line that may be used with the present invention.
Figure 4:
FIG. 4 is a cross-sectional view of a second embodiment of an irrigation line that may be used with the present invention.
Figure 5:
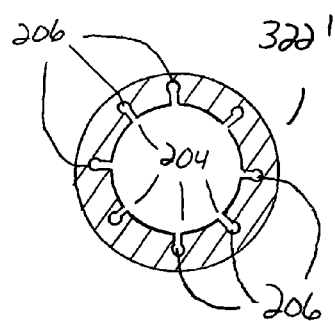
FIG. 5 is a cross-sectional view of a third embodiment of an irrigation line that may be used with the present invention.
Figure 6:
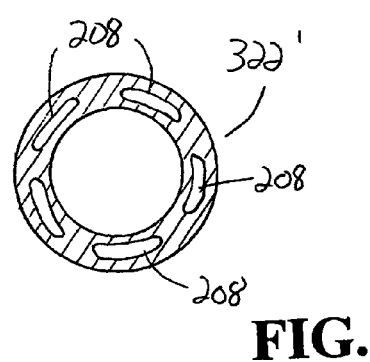
FIG. 6 is a cross-sectional view of a fourth embodiment of an irrigation line that may be used with the present invention.

Compliance in irrigation line 322' can be increased by reducing the stiffness of irrigation line 322'. As best seen in FIGS. 3-6, reducing the stiffness of irrigation line 322' can be accomplished by varying the cross-section of irrigation line 322. For example, FIG. 3 illustrates irrigation line 322' having a plurality of external weakened areas or slits 200. Slits 200 increase the compliance of irrigation line 322' and are compatible with internal connectors, such as barbed fittings. FIG. 4 illustrates irrigation line 322' having a plurality of internal weakened areas or slits 202. Slits 202 increase the compliance of irrigation line 322' and are compatible with external connectors, such as sockets. FIG. 5 illustrates irrigation line 322' having a plurality of internal weakened areas or slits 204 terminating in pockets 206. Slits 204 increase the compliance of irrigation line 322' and are compatible with internal connectors, such as barbed fittings. Pockets 206 entrain air, further increasing the compliance of irrigation line 322'. FIG. 6 illustrates irrigation line 322' having a plurality of internal weakened areas or pockets 208 that entrain air, increasing the compliance of irrigation line 322'. Alternatively, line 325 can be co-extruded so that irrigation line 322 is made from a softer (lower durometer) material than aspiration line 324. For example, irrigation line 322 may be made from a material having a stiffness on the order of 30 shore A to 70 shore A durometer.

Alternatively, as shown in FIGS. 7-9, irrigation lines 422 and 522 may have relatively thin walls 424 and 524, respectively. Reducing the thickness of walls 424 and 524 increases the flexibility of walls 424 and 524, thereby adding compliance to irrigation lines 422 and 522. To prevent irrigation lines 422 and 522 from collapsing, such as when bent of kinked, irrigation lines 422 and 522 contain internal anti-collapse features 426 and 526, respectively. For example, as seen in FIGS. 7 and 8, internal feature 426 may be shaped as longitudinal, opposing ribs. As seen in FIG. 9, feature 526 may be formed as longitudinal webbing or cross-bracing.

This description is given for purposes of illustration and explanation. It will be apparent to those skilled in the relevant art that changes and modifications may be made to the invention described above without departing from its scope or spirit.

We claim:

1. A surgical system, comprising:
   a) a surgical console;
   b) a handpiece; and
   c) an irrigation line and an aspiration line connecting the handpiece to the console, the irrigation line containing a plurality of weakened areas, the weakened areas increasing compliance of the irrigation line relative to the aspiration line;
   wherein the weakened areas comprise slits in walls of the irrigation line which are configured to be flexibly open to the irrigation line such that irrigation fluid at least partially flows into the weakened areas during irrigation.

2. The system of claim 1 wherein the slits comprise internal slits.

3. The system of claim 1 wherein the slits further comprise external slits.

4. The system of claim 2 wherein the internal slits terminate in pockets.

5. The system of claim 1 wherein the weakened areas further comprise internal air pockets.

6. A surgical system, comprising:
   a) a surgical console;
   b) a handpiece; and
   c) an irrigation line and an aspiration line connecting the handpiece to the console, wherein at least a portion of the irrigation line and at least a portion of the aspiration line are co-extruded and wherein at least a portion of the co-extruded irrigation line portion is formed from a material having a lower durometer than a material used to form the co-extruded aspiration line portion.

7. The system of claim 6, wherein the material used to form the irrigation line has a stiffness of between 30 shore A to 70 shore A durometer.

8. The system of claim 7, wherein the material used to form the aspiration line has a stiffness of between 75 shore A to 100 shore A durometer.

9. The system of claim 6, wherein the material used to form the aspiration line has a stiffness of between 75 shore A to 100 shore A durometer.

10. The surgical system of claim 6, wherein the portion of the irrigation line and the aspiration line that are coextruded are connected to the handpiece.

11. The surgical system of claim 6, wherein a cross section of the co-extruded aspiration line portion and co-extruded irrigation line portion together form a figure eight.

12. A surgical system, comprising:
   a) a surgical console;
   b) a handpiece;
   c) an irrigation line and an aspiration line, each with circular cross sections, connecting the handpiece to the console, wherein at least a portion of the irrigation line and at least a portion of the aspiration line are co-extruded and wherein at least a portion of the co-extruded irrigation line portion is formed from a material having a lower durometer than a material used to form the co-extruded aspiration line portion; and
   wherein an outer wall of the co-extruded aspiration line portion is thicker than an outer wall of the co-extruded irrigation line portion.

13. The surgical system of claim 12, wherein a co-extruded wall between the irrigation line and the aspiration line is thicker than an outer wall of the irrigation line.

14. The surgical system of claim 12, wherein a cross section of the co-extruded aspiration line portion and co-extruded irrigation line portion together form a figure eight.

15. The surgical system of claim 12, wherein a cross section of the co-extruded aspiration line portion has a smaller diameter than a diameter of the co-extruded irrigation line portion.

* * * * *